(12) United States Patent
Houston (10) Patent No.: US 10,478,570 B2
(45) Date of Patent: *Nov. 19, 2019

(54) MEDICATION DELIVERY APPARATUS AND ACCOMPANYING SYSTEM FOR THE APPLICATION OF LOCAL ANESTHETICS TO A TREATMENT SITE AND METHOD FOR USE OF SAME

(71) Applicant: Dualams, Inc., Dallas, TX (US)

(72) Inventor: John S. Houston, Dallas, TX (US)

(73) Assignee: Dualams, Inc., Dallas, TX (US)

( * ) Notice: Subject to any disclaimer, the term of this patent is extended or adjusted under 35 U.S.C. 154(b) by 959 days.

This patent is subject to a terminal disclaimer.

(21) Appl. No.: 14/330,359

(22) Filed: Jul. 14, 2014

(65) Prior Publication Data
US 2015/0209529 A1 Jul. 30, 2015

Related U.S. Application Data

(60) Provisional application No. 61/933,654, filed on Jan. 30, 2014.

(51) Int. Cl.
*A61M 11/00* (2006.01)
*A61M 5/00* (2006.01)
(Continued)

(52) U.S. Cl.
CPC ............ *A61M 11/005* (2013.01); *A61M 5/00* (2013.01); *A61M 16/104* (2013.01);
(Continued)

(58) Field of Classification Search
None
See application file for complete search history.

(56) References Cited

U.S. PATENT DOCUMENTS 3,291,122 A * 12/1966 Engstrom ......... A61M 16/0081
128/200.16
3,561,444 A * 2/1971 Boucher ........... A61M 15/0085
128/200.16

(Continued)

FOREIGN PATENT DOCUMENTS

WO    WO2009035646    3/2009

OTHER PUBLICATIONS

International Searching Authority, International Search Report, PCT/US2015/013506, dated May 11, 2015.

*Primary Examiner* — Kathryn E Ditmer
(74) *Attorney, Agent, or Firm* — Scott T. Griggs; Griggs Bergen LLP (57) ABSTRACT

A medication delivery apparatus and system for the application of a local anesthetic to a treatment site, such as an airway, and method for use of same are disclosed. In one embodiment of the medication delivery apparatus and system, a reservoir supplies a local anesthetic to a lower chamber of a housing wherein an ultrasonic transducer applies ultrasonic energy thereto, thereby nebulizing the local anesthetic. A control valve is interposed between a source of positive pressure air and an upper chamber of the housing to selectively apply positive air pressure to the upper chamber. Upon the application of positive air pressure, the airflow delivers the nebulized anesthetic to a patient's airway by way of a laryngoscope side port coupling, laryngoscope vacuum port coupling, or catheter coupling, for example. The application of local anesthetic, itself, in this nebulized manner mitigates gaging, chocking, aspirating, bucking and laryngospasms.

24 Claims, 5 Drawing Sheets

(51) Int. Cl.
  *A61M 16/10* (2006.01)
  *A61M 16/20* (2006.01)
  *A61M 16/08* (2006.01)

(52) U.S. Cl.
  CPC ....... *A61M 16/109* (2014.02); *A61M 16/0816* (2013.01); *A61M 16/201* (2014.02); *A61M 2202/0241* (2013.01); *A61M 2205/50* (2013.01); *A61M 2210/1028* (2013.01); *A61M 2210/1032* (2013.01)

(56) References Cited

U.S. PATENT DOCUMENTS

| | | | |
|---|---|---|---|
| 3,565,072 A * | 2/1971 | Gauthier | A61G 10/02 128/200.16 |
| 3,901,443 A * | 8/1975 | Mitsui | B05B 17/0615 239/102.2 |
| 3,918,640 A * | 11/1975 | Piccino | B05B 17/0615 239/4 |
| 4,008,716 A * | 2/1977 | Amlong | A62B 9/02 128/205.24 |
| 4,014,637 A * | 3/1977 | Schena | F23C 13/00 261/121.1 |
| 4,253,468 A | 3/1981 | Lehmbeck | |
| 4,384,570 A * | 5/1983 | Roberts | A61B 1/07 600/185 |
| 4,534,343 A | 8/1985 | Nowacki et al. | |
| 4,776,990 A * | 10/1988 | Verity | B05B 7/162 128/200.16 |
| 4,803,977 A * | 2/1989 | Kremer, Jr. | A61B 5/0813 128/200.18 |
| 4,882,096 A * | 11/1989 | Rueben | B05B 17/0607 261/30 |
| 4,926,852 A | 5/1990 | Zoltan et al. | |
| 5,211,890 A * | 5/1993 | Wentworth, Jr. | F02M 25/0224 261/30 |
| 5,226,411 A * | 7/1993 | Levine | A61M 16/1085 128/203.26 |
| 5,368,016 A | 11/1994 | Henry | |
| 5,551,416 A * | 9/1996 | Stimpson | A61M 15/0085 128/200.14 |
| 5,593,661 A | 1/1997 | Henry | |
| 5,599,297 A * | 2/1997 | Chin | A61M 13/003 604/26 |
| 5,803,078 A * | 9/1998 | Brauner | A61M 16/04 128/200.14 |
| 5,922,247 A * | 7/1999 | Shoham | B05B 17/0615 239/102.2 |
| 5,954,688 A | 9/1999 | Adams et al. | |
| 6,701,928 B2 | 3/2004 | Rubin et al. | |
| 7,204,248 B2 * | 4/2007 | Enk | A61M 11/06 128/200.14 |
| 7,452,523 B2 | 11/2008 | Hofmann et al. | |
| 7,998,463 B2 | 8/2011 | Hofmann et al. | |
| 8,156,933 B2 * | 4/2012 | Raghuprasad | A61M 15/0065 128/200.14 |
| 8,555,874 B2 | 10/2013 | Fink et al. | |
| 2006/0201502 A1 * | 9/2006 | Lieberman | A61M 11/005 128/204.14 |
| 2006/0213508 A1 * | 9/2006 | Murray | B05B 17/0615 128/200.16 |
| 2008/0202550 A1 | 8/2008 | McDermott et al. | |
| 2010/0055600 A1 * | 3/2010 | Norikane | G03G 9/0802 430/111.4 |
| 2011/0108025 A1 * | 5/2011 | Fink | A61M 11/005 128/200.16 |
| 2011/0120456 A1 * | 5/2011 | Immel | A61M 15/0085 128/200.23 |
| 2011/0147482 A1 * | 6/2011 | Matsuura | B01D 1/14 239/102.1 |
| 2012/0048266 A1 * | 3/2012 | Alelov | A61M 11/005 128/202.21 |
| 2012/0125334 A1 * | 5/2012 | Korneff | A61M 11/005 128/203.26 |
| 2012/0160237 A1 * | 6/2012 | Flickinger | A61M 3/025 128/200.23 |
| 2013/0064683 A1 * | 3/2013 | Oshima | F04B 23/04 417/44.1 |
| 2013/0079733 A1 * | 3/2013 | Burt | B05B 7/0012 604/290 |
| 2013/0267864 A1 * | 10/2013 | Addington | A61B 5/4839 600/538 |
| 2013/0274550 A1 | 10/2013 | Takeuchi | |
| 2014/0109899 A1 * | 4/2014 | Boucher | A61M 11/06 128/200.18 |
| 2014/0166038 A1 * | 6/2014 | Leung | A45D 1/04 132/221 |
| 2014/0352689 A1 * | 12/2014 | Seshadri | A61M 15/0085 128/200.16 |

* cited by examiner

MEDICATION DELIVERY APPARATUS AND ACCOMPANYING SYSTEM FOR THE APPLICATION OF LOCAL ANESTHETICS TO A TREATMENT SITE AND METHOD FOR USE OF SAME

PRIORITY STATEMENT AND CROSS REFERENCE TO RELATED APPLICATIONS

This application claims priority from patent application U.S. Patent Application Ser. No. 61/933,654 entitled "Medication Delivery Apparatus and Accompanying System for the Application of Local Anesthetics to an Airway and Method for Use of Same" and filed on Jan. 30, 2014 in the name of John S. Houston; which is hereby incorporated by reference for all purposes.

TECHNICAL FIELD OF THE INVENTION

This invention relates, in general, to systems and methods of treatment of the living body and apparatus used in the inspection and treatment of diseases, wounds, and other abnormal conditions of the bodies of humans, and in particular, to a medication delivery apparatus and accompanying system for the application of local anesthetics to a treatment site and a method for use of the same.

BACKGROUND OF THE INVENTION

Without limiting the scope of the present invention, the background will be described in relation to treatment of airways, as an example. An adverse physiological response to laryngoscopic examination and the performance of procedures on the larynx, trachea, and related anatomical parts of a patient is common. More specifically, tactile stimulation of receptors in the pharynx, hypopharynx, vocal cords, tracheal mucosa and other areas related to an airway often results in reflex gagging, coughing, aspiration, bucking and laryngospasm, for example. Accordingly, laryngoscopic examination and the performance of various procedures is typically performed under local anesthesia by the application of lidocaine directly onto the larynx. The application of local anesthetic, itself, in this manner often causes the patient to gag, chock, aspirate, buck and laryngospasm. That is, the application of the local anesthetic causes many of the problems it is intended to prevent. Accordingly, a need exists for improvements in the application of local anesthesia prior to laryngoscopic examination and related procedures. Further, such need exists beyond the treatment of airways.

SUMMARY OF THE INVENTION

It would be advantageous to achieve advances in medical delivery instrumentation to improve the application of local anesthesia prior to laryngoscopic examination and related procedures. It would also be desirable to enable a mechanical solution that would improve medical science and technique such that the application of local anesthetic, itself, does not cause the patient to gag, chock, aspirate, buck or laryngospasm. Further, it would be desirous to develop solutions that extend beyond the treatment of airways. To better address one or more of these concerns, a medication delivery apparatus and system for the application of a local anesthetic to a treatment site, such as an airway, and method for use of same are disclosed. In one embodiment of the medication delivery apparatus, a reservoir supplies a local anesthetic to a lower chamber of a housing wherein an ultrasonic transducer applies ultrasonic energy thereto, thereby nebulizing the local anesthetic. A control valve is interposed between a source of positive pressure air and an upper chamber of the housing to selectively apply positive air pressure to the upper chamber. Upon the application of positive air pressure, the airflow delivers the nebulized anesthetic to a patient's airway by way of a laryngoscope side port coupling, laryngoscope vacuum port coupling, or catheter coupling, for example. The application of local anesthetic, itself, in this nebulized manner mitigates gaging, chocking, aspirating, bucking and laryngospasms.

In one embodiment of the medication delivery system, a flexible endoscope having a flexible tubular member having an insertion tip for insertion into an orifice, such as an airway is utilized in combination with the medication delivery apparatus. The various operational states of the medication delivery apparatus are selectively actuated during the selectively bending of the flexible tubular member. The medication delivery system provides for coordinated control of the movement or bending of the flexible endoscope and selective control of the application of the local anesthetic. Therefore, the location and amount of local anesthetic applied may be metered to a particular location. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIGS. 3A through 3C are side schematic elevation views of the medication delivery apparatus depicted in FIGS. 1A and 1B, wherein FIG. 3A depicts the medication delivery apparatus in an OFF state, FIG. 3B depicts the medication delivery apparatus in a STANDBY state, and FIG. 3C depicts the medication delivery apparatus in an ON state; and FIGS. 4A and 4B are side schematic elevation views of another embodiment of the medication delivery apparatus depicted in FIGS. 1A and 1B, wherein FIG. 4A depicts the medication delivery apparatus being loaded and FIG. 4B depicts the medication delivery apparatus loaded and ready for operation.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figures 1A, 1C:
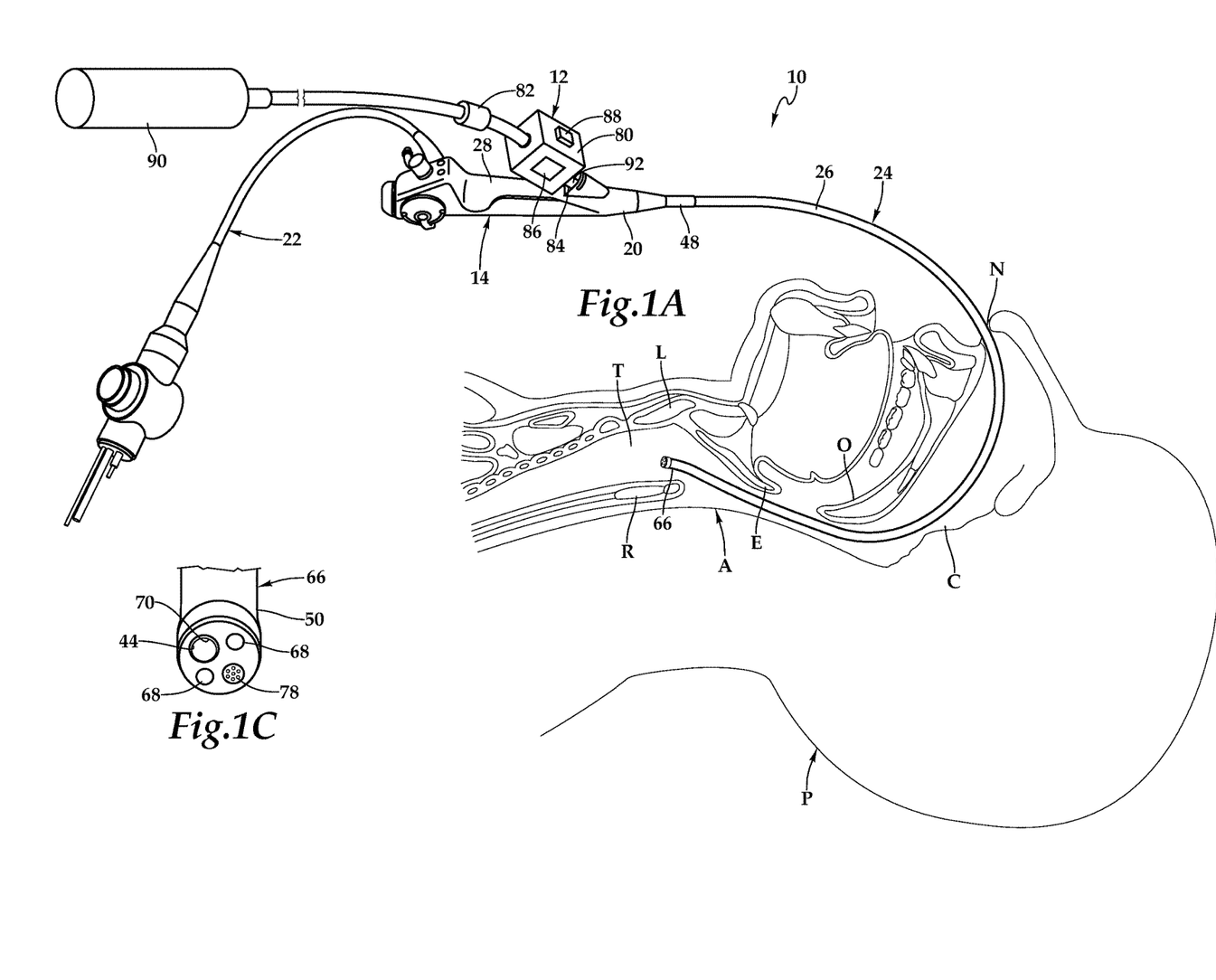
FIG. 1A is a side elevation view of one embodiment of a medication delivery system, including a flexible endoscope and medication delivery apparatus, for the application of local anesthetics to a treatment site, such as an airway, being utilized according to the teachings presented herein on a patient, the airway of which is depicted in cross-section.
FIG. 1C is a front perspective view of a portion of the medication delivery system depicted in FIG. 1A.
Figure 1B:
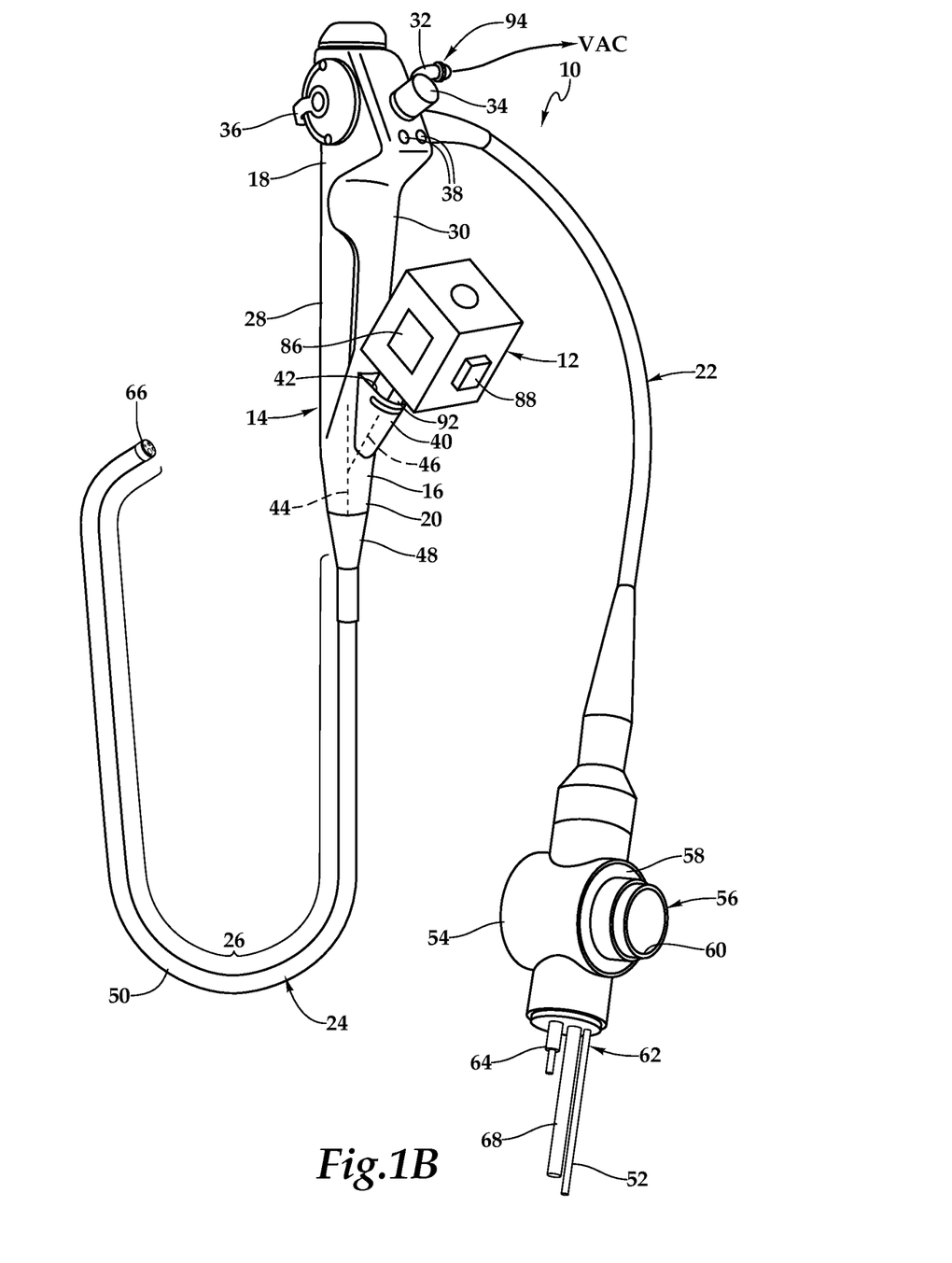
FIG. 1B is a front elevation of the medication delivery system depicted in FIG. 1A.

Referring initially to FIGS. 1A through 1C, therein is depicted a medication delivery system for the application of local anesthetics that is schematically illustrated and generally designated 10. As shown, the medication delivery system 10, which includes a medication delivery apparatus 12 and a flexible endoscope 14, is applying the local anesthetic to a patient P, and more particularly, an airway A of the patient P, with the use of the flexible endoscope 14. It should be appreciated that the teachings presented herein are not limited to the treatment of an airway, rather the teachings are applicable to an orifice and treatment site, including ear channels, rectums, lungs, and vaginas, for example.

The flexible endoscope 14 is principally constructed of an operational section 16 having ends 18, 20. A universal cord 22 extends from the operational section 16 at the end 18 and an insertion portion 24, which may be a flexible tubular member 26, is connected to the end 20 of the operational section 16. The operational section 16 includes a body 28 having a grasping portion 30 configured for an operator's grip, between the ends 18, 20. At the 18 end, a vacuum port 32 is provided as are various operational control members 34. As shown, in one embodiment, the various operational control members 34 may include a bending lever 36 that performs bending operations of the insertion portion 24. An operation control cluster 38 provides for performing air/water feeding or suction operations or various operations related to imaging and illumination, for example. A treatment insertion section 40 is located near the grasping portion 30 on the body 28 and includes a treatment insertion port 42 for inserting various instruments therethrough, including through a treatment insertion channel tube 44 inside the operating section which is accessed via a branching member 46. A bend preventing portion 48 is located at the end 20 of the operational section 16.

The universal cord 22 may be a composite cable 50 that allows the insertion therethrough of various signal lines, including a light guide source 52, for example. More particularly, the universal cord 22 includes an endoscope connector 54 that is configured to include an electronic connection portion 56 on a side portion 58 thereof to which an electric cable 60 for connection with a video processor may be connected. A light source connector portion 62 is provided for connection to a fiber optic cable and an air/water feeding plug 64 connects the air/water feeding tube with an air/water feeding apparatus.

As mentioned, the insertion portion 24 includes the flexible tube portion or flexible tubular member 26 that may be a tubular member formed with flexibility so as to be passively bendable. As shown, an insertion tip 66 includes light sources 68, an exit opening 70 to the treatment insertion channel tube 44, and a camera lens 78, which provides optics video to the location of treatment site and is positioned and communicates with the universal cord 22.

The medication delivery apparatus 12 includes a housing 80 having an air pressure coupling 82 and a medical device coupling 84. An access door 86 provides selective access to a re-fillable supply of local anesthetic therein. In one embodiment, the local anesthetic may be lidocaine and, by way of example and not by way of limitation, 4% lidocaine. As depicted, the medication delivery apparatus 12 is battery powered. It should be appreciated, however, that the medication delivery apparatus 12 may be powered by a conventional plug or other technology. A controller 88 controls the operation of the medication delivery apparatus 12. As shown, an air pressure supply 90 is coupled to the air pressure coupling 82. Further, the medical device coupling 84, which includes a tubular connector 92, secures the medication delivery apparatus 12 to the flexible endoscope 14 at the treatment insertion port 42.

It should be appreciated that although one particular flexible endoscope is depicted, the medication delivery apparatus presented herein may be employed with a variety of types of flexible endoscopes. Moreover, the coupling between the medication delivery apparatus and the flexible endoscope may vary. For example, the medication delivery apparatus may couple to the flexible endoscope at a vacuum port, such as the vacuum port 32. Such a connection is illustrated by arrow 94. Further, a catheter or other tubular member may be utilized to couple the medication delivery apparatus 12 to the flexible endoscope 14.

In operation, as shown, the insertion portion 24 of the flexible endoscope 14 is guided into the airway A of the patient P initially through the nasal opening N, which is superior to the oral cavity O. As depicted, the insertion tip 66 of the flexible endoscope 14 passes by the conchae C and epiglottis E to a portion of the airway A proximate to the laryngeal prominence L and cricoid cartilage R at the trachea T. As alluded, the bending lever 36 may be manually manipulated by an operator to guide the flexible endoscope 14. It should be appreciated that flexible endoscopes have various entries and uses in terms of a patient's body and medicine. Therefore, the illustrated approach does not limit other techniques that may be used with the medication delivery system 10 presented herein.

Local anesthetic is applied via the selective positioning of the insertion tip 66 and actuation of the medication delivery apparatus 12 by controller 88. When the audio/visual system shows the insertion tip 66 is at the desired location, the controller 88 is actuated to provide a metered amount of local anesthetic for a controlled duration. The local anesthetic leaves the medication delivery apparatus 12 as nebulized local anesthetic carried by compressed air or another gas, for example. Depending on the configuration of the coupling between the medication delivery apparatus 12 and the flexible endoscope 14, the nebulized local anesthetic, for example travels through the treatment insertion port 42 and through the treatment channel tube 44 via the branching member 46. The nebulized local anesthetic exits the exit opening 70 of the insertion tip 66 of the insertion portion 24.

Figure 2A:
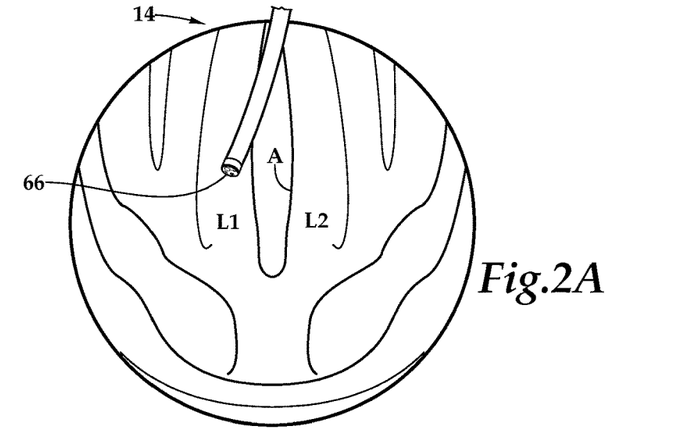
FIGS. 2A through 2C are top plan views of the medication delivery system presented in FIGS. 1A through 1C being utilized, in one embodiment, on deep vocal folds of the patent.
Figure 2B:
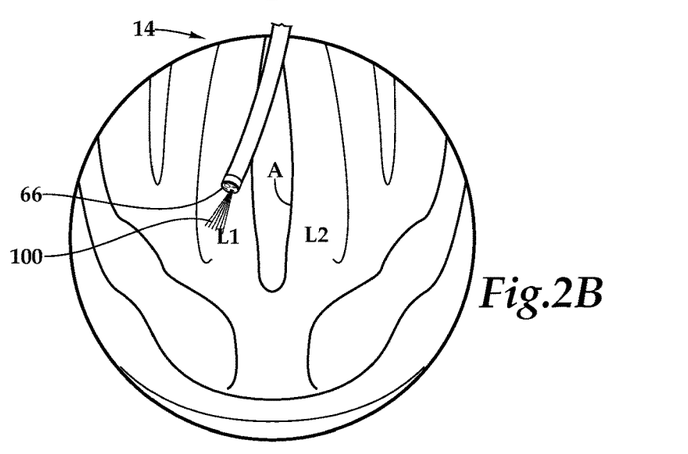
Figure 2C:
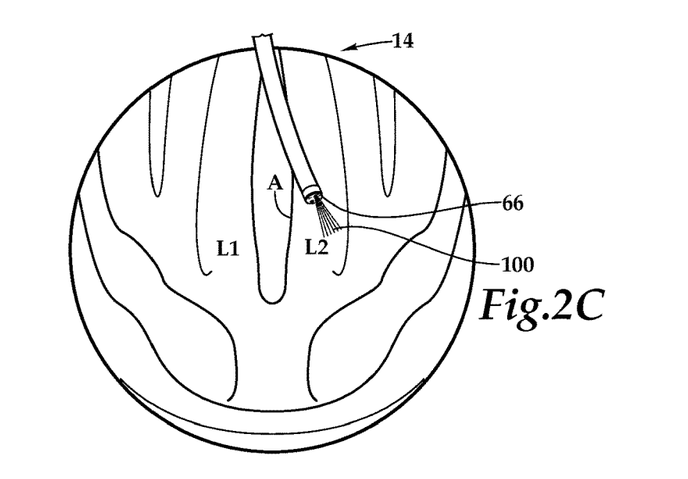

FIGS. 2A through 2C depict the medication delivery system 10 being utilized on deep vocal folds L1, L2 within the airway A of the patient P. As shown, the medication delivery system 10 and, in particular, the insertion portion 24 of the flexible endoscope 14 is positioned in the airway A of the patient P such that the insertion tip 66 is positioned proximate to the vocal fold L1 in FIGS. 2A and 2B and proximate to the vocal fold L2 in FIG. 2C. In FIG. 2A, local anesthetic is not provided. In this operational state, a nebulized local anesthetic is produced within the medication delivery apparatus 12, which remains in the medication delivery apparatus 12.

Figure 3A:
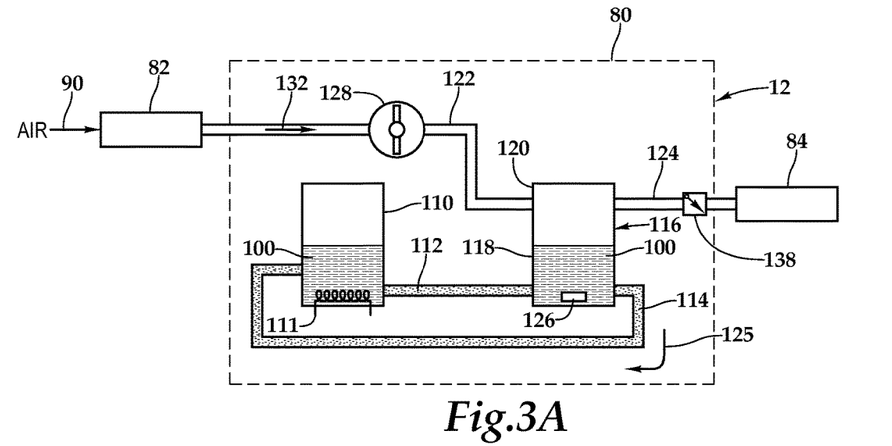
Figure 3B:
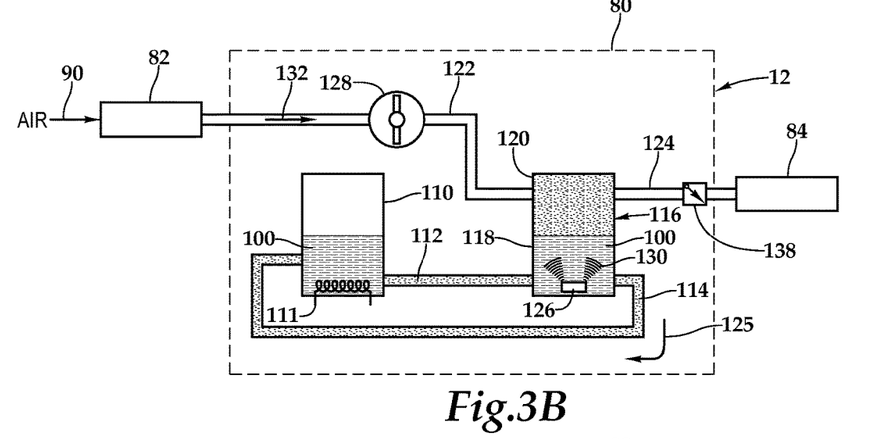
Figure 3C:
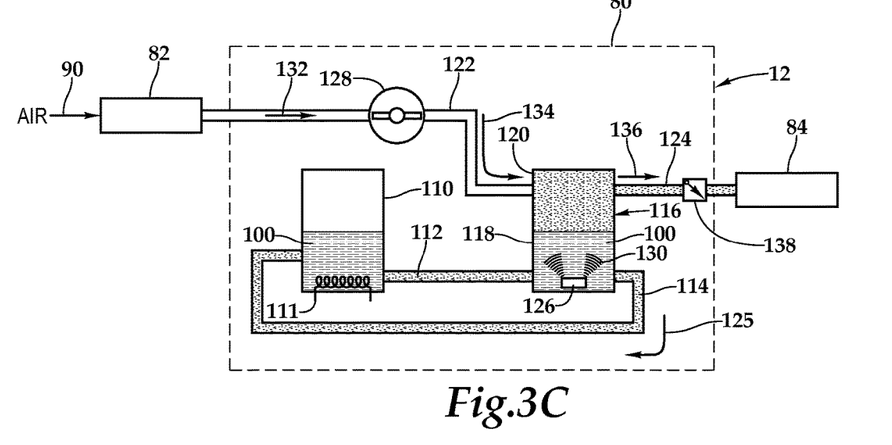

In FIG. 2B, however, the medical delivery system provides a metered amount of local anesthetic for a controlled duration of time as shown by nebulized local anesthetic 100. As previously discussed, the nebulized local anesthetic 100 is delivered from the medication delivery apparatus 12 to the flexible endoscope 14 and, in particular, the treatment channel tube 44 of the insertion portion 24, where the nebulized local anesthetic 100, which may be lidocaine or other suitable anesthetic, exits the flexible endoscope 14 at exit opening 70. In the nebulized form described herein, the local anesthetic 100 is visible and, in particular, visible in using the optical capabilities of the endoscope 12. Following the delivery of the controlled amount of nebulized local anesthetic, no anesthetic is provided as the flexible endoscope 14 is repositioned to a location proximate vocal fold L2, as shown in FIG. 2C. At FIG. 2C, a metered amount of nebulized local anesthetic 100 is provided in a manner that permits the local anesthetic to be visibly painted onto the treatment site in a controlled manner. In these operational states whereby, the local anesthetic supplied to the medication delivery apparatus 12 is nebulized and carried by the application of air into the airway A of the patient P.

It should be appreciated that the various operational states of the medication delivery apparatus 12 are selectively actuated during the selectively bending of the flexible tubular member 24. As previously discussed, an adverse physiological response to laryngoscopic examination and the performance of procedures on the larynx, trachea, and related anatomical parts of a patient, such as the patient P, is common. More specifically, tactile stimulation of receptors in the pharynx, hypopharynx, vocal cords, tracheal mucosa and other areas related to the airway A often results in reflex gagging, coughing, aspiration, bucking and laryngospasm, for example. Accordingly, laryngoscopic examination and the performance of various procedures is typically performed under local anesthesia by the application lidocaine directly onto the larynx. By way of the medication delivery system, the application of local anesthetic, itself, mitigates gagging, chocking, aspirating, bucking or laryngospasms in a patient as the delivery of the local anesthetic is in a controllable metered and nebulized form; rather than an uncontrollable stream of a liquid.

Referring now to FIGS. 3A through 3C, wherein the medication delivery apparatus 12 is depicted in additional detail. More particularly, FIG. 3A depicts the medication delivery apparatus 12 in an OFF state, FIG. 3B depicts the medication delivery apparatus 12 in a STANDBY state, and FIG. 3C depicts the medication delivery apparatus 12 in an ON state. The medical delivery apparatus 12 includes a reservoir 110 configured to contain the local anesthetic 100, which is referred to as local anesthetic 100 whether in a liquid or nebulized state. The reservoir may include a volume from about 5 ml to about 200 ml. A heating element 111 may be associated with the reservoir 110 and positioned at the bottom thereof. In one embodiment, the heating element 111 is configured to heat the local anesthetic to a temperature that is comfortable and appropriate for contact with the airway A of the patient P. In one implementation, the heating element 111 may heat the local anesthetic to a temperature from about 50° F. (10° C.) to about 105° F. (40.5° C.). By way of example and not by way of limitation, the heating element 111 may be a heating coil. As shown, the reservoir 110 is disposed in fluid communication with a supply channel 112 and a circulation channel 114. A nebulization housing 116 includes a lower chamber 118 and an upper chamber 120. In one implementation, the lower chamber 118 and the upper chamber 120 form integral portions of the nebulization housing 116. The lower chamber 118 is disposed in fluid communication with the supply channel 112 and the circulation channel 114. A fluid circuit 125 is thereby formed by the flow of local anesthetic from the reservoir 110 to the supply channel 112 to the lower chamber 118 to the circulation channel 114. Further, in one embodiment, the heating element may be associated with the lower chamber 118, supply channel 112 or the circulation channel 114, for example.

The upper chamber 120 is disposed in fluid communication with an airflow channel 122 and a delivery channel 124. An ultrasonic transducer 126 is positioned in the lower chamber 118 in order to generate, upon energization, ultrasonic energy, which nebulizes the local anesthetic 100. In one implementation, the ultrasonic transducer 126 may be a piezoelectric transducer that provides ultrasonic waves. In particular, by way of example and not by way of limitation the piezoelectric transducer may be a 40 KHz to about 2.5 MHz. A control valve 128 is interposed between a source of positive pressure air connected to air pressure coupling 82 and the airflow channel 122. In one embodiment, the control valve may be a 0.2 lbs to 250 lbs pressure regulator and the source of positive pressure air may be an air compressor or storage tank. In one implementation, the source of positive air pressure provides air pressure from about 0.2 psi to about 25 psi. As shown, by a comparison of FIGS. 3A through 3C, the control valve 128, which is manipulated by the controller 88, is configured to selectively apply air to the airflow channel 122. A medical device coupling 84 is located at a distal end of the delivery channel 124. In one implementation, the medical device coupling 84 may be selected from the group of laryngoscope side port couplings, laryngoscope vacuum port couplings, and catheter couplings.

Referring now to FIG. 3A, in an OFF operational state, the local anesthetic 100 remains in the reservoir 110 and is not circulated from the reservoir 110 to the lower chamber 118. Further, the source of air pressure is not providing positive air pressure to the upper chamber 120 of the nebulization housing 116 as the control valve 128 is set to block airflow therethrough. As shown by arrow 132, the air flow only reaches the control valve 128 and does not pass therethrough. Referring now to FIG. 3B, in a STANDBY operational state, the local anesthetic 100 is circulated initially from the reservoir 110, where heating element 111 provides heat such that the local anesthetic 100 will be an agreeable and appropriate temperature to patient P. From the reservoir 110, the local anesthetic 100 continues through the fluid circuit 125 to the lower chamber 118, wherein the ultrasonic transducer applies ultrasonic energy 130 to the local anesthetic 100, thereby producing a nebulized local anesthetic 100 which remains in the upper chamber 120. In this operational state, the control valve 128 is positioned to block the flow of air from the source of pressurized air 90 to the upper chamber 120 and the delivery channel 124. As shown, the fluid circuit 125 provides a return path for the local anesthetic 100 from the nebulization housing 116 to the reservoir 110 via the circulation channel 114. It should be appreciated that the reservoir 110 may be accessed by access door 86 to re-fill the supply of anesthetic. Further, various electronic elements such as a power supply may be included with the medication delivery apparatus 12, but are not shown.

Referring now to FIG. 3C, the medication delivery apparatus 12 is in an ON operational state, wherein the local anesthetic 100 is circulated from the reservoir 110 to the lower chamber 118 of the nebulization housing 116 through the fluid circuit 125. Within the lower chamber 118 of the nebulization housing 116, the ultrasonic transducer 126 applies ultrasonic energy 130 to the local anesthetic 100, thereby producing a nebulized local anesthetic 100 which is carried by the application of air, as shown by arrows 132, 134 to the delivery channel 124, as shown by arrow 136. In this operational state, the control valve 128 permits the flow of pressurized air from the air source to the upper chamber 120 and the delivery channel 124 and onto the airway A of the patient P, for example. As shown by comparing FIGS. 3B and 3C, via the controller 88 and control valve 128, the application of local anesthetic may be selectively controlled to provide targeted and metered amounts of local anesthetic. It should be appreciated that although not shown, the control valve 128 may be under the control of the controller 88.

In one particular embodiment, a valve 138, which may be a check valve, is positioned within the delivery channel 124. In the presence of negative pressure from the medical device coupling 84, the valve 138 closes in order to prevent the local anesthetic 100 from being pulled out of the housing 80 of the medication delivery apparatus 12. In one application, as alluded to, the medication delivery apparatus 12 may be coupled to the flexible endoscope 14 at the treatment insertion section 40. In this configuration, a vacuum (VAC), see FIG. 1B, may be applied at the vacuum port 32 and via control of the vacuum (VAC), the medication delivery apparatus 12 may be operated between the ON operational state and an EFFECTIVE STANDBY operational state, whereby the presence of the negative pressure by way of the vacuum port 32 causes the valve 138 to close and prevents the flow of the local anesthetic 100 from exiting the delivery channel 124. That is, the ON operational state and the EFFECTIVE STANDBY operational state are selected by the state of the valve 138 such that the valve 138 closing in response to negative pressure at the vacuum port 32, e.g., the application of a vacuum (VAC) causes the EFFECTIVE STANDBY operational state.

In other conditions, if power is provided to the medication delivery apparatus 12, then the ON operational state is selected. Further, in this implementation with the medication delivery apparatus 12 coupled to the flexible endoscope 14 at the treatment insertion port 42 to provide for use of a vacuum (VAC) at the vacuum port 32, the action of the vacuum (VAC) performs the additional function of removing an excess local anesthetic 100 and/or other bodily fluids during actuation at the EFFECTIVE STANDBY operational state. This provides additional medical efficacy.

Figure 4A:
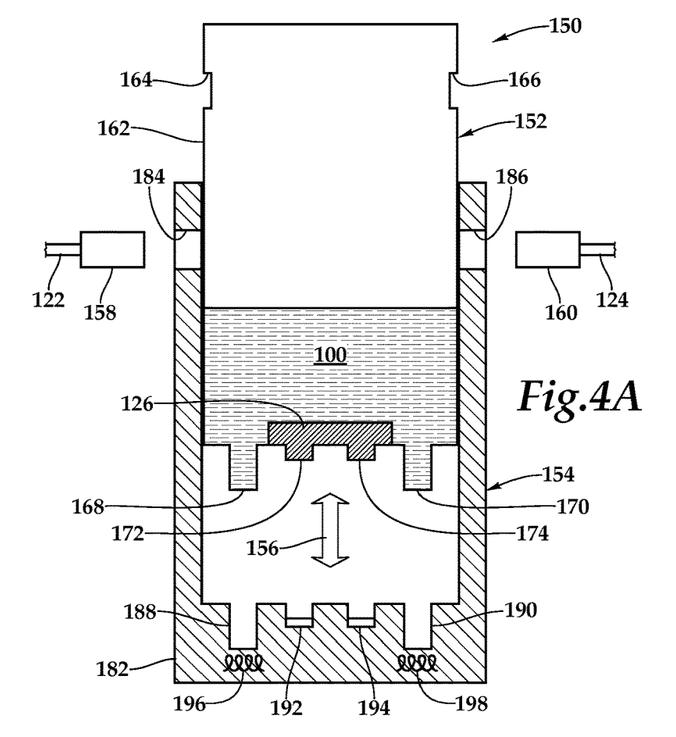
Figure 4B:
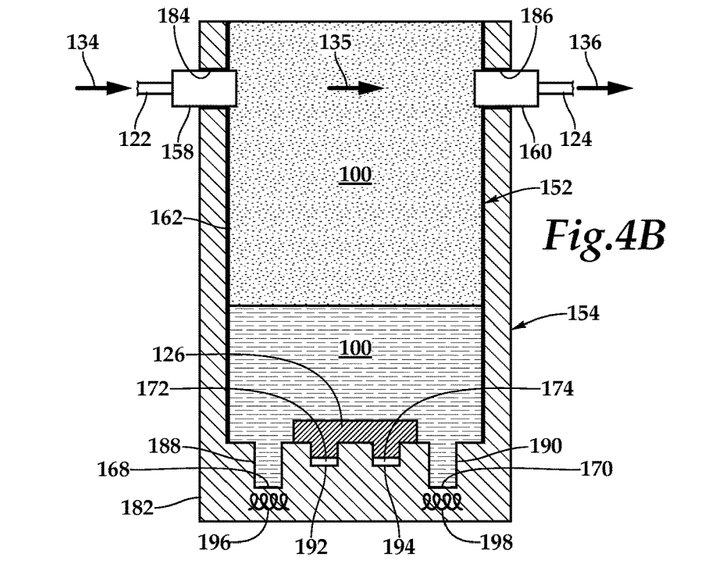

Referring now to FIGS. 4A and 4B, another embodiment of a medication delivery apparatus 150 for the application of a local anesthetic to a treatment site is shown. An inner housing 152 is releasably engageable with an outer housing 154 as shown by arrow 156. Upon engagement, coupling member 158, which is connected to the airflow channel 122, and coupling member 160, which is connected to the delivery channel 124 may be connected to the medication delivery apparatus 150. As previously discussed, a medical device coupling may be located at a distal end of the delivery channel 124. In one implementation, the medication delivery apparatus 150 provides a disposable inner housing 152, which contains a measure of the local anesthetic, that is releasably engageable with the outer housing 154. After a use, the inner housing 152 may be removed and a new inner housing or cartridge may be loaded.

With respect to the inner housing 152, an exterior wall 162, which defines a reservoir, has a sidewall and base and includes openings 164, 166 therethrough. Mechanical connectors 168, 170 extend from the exterior wall 162 in order to form a mechanical connection with the outer housing 154. By way of example, and not by way of limitation, the mechanical connection may be a bayonet connection, a male-female pin and box connection, snap-fit engagement, or other type of connection. The ultrasonic transducer 126 is located within the interior housing 152 and includes prongs 172, 174 extending therefrom. As previously discussed, the ultrasonic transducer 126 is configured to generate, upon energization, ultrasonic energy. In one implementation, the prongs 172, 174 coupled the ultrasonic transducer 126 to a source of power within the outer housing 154.

The outer housing 154 includes a receiving chamber 182 with openings 184, 186 traversing therethrough to provide for mating connections with the coupling members 158, 160. Receivers 188, 190 are positioned to receive the mechanical connectors 168, 170 and form a releasable connection therewith. Receivers 192, 194 mate with the prongs 172, 174 to provide the aforementioned source of power to the ultrasonic transducer 126. In one implementation, the prongs 172, 174 and the receivers 192, 194 are not required as the ultrasonic transducer 126 includes a power supply, such as a battery that may be actuated by a button or other feature on the outer housing 154. Heating elements 196, 198 may be positioned within the outer housing to selectively supply a source of heat to the local anesthetic 100. Similar to the power supply, the heating source may be included in the inner housing 152 in another embodiment.

In operation, the inner housing 152 is configured to insert into the receiving chamber 182 of the outer housing 154 and releasably engage therewith, thereby defining an engaged position between the inner housing 152 and the outer housing 154. In the engaged position, the upper channel, as defined by arrows 134, 135, and 136, is disposed in fluid communication with the airflow channel 122 and the delivery channel 124. In a first operational state, such as ON, of the medication delivery apparatus 150, a source of positive pressure air traverses the upper channel, as represented by arrows 134, 135, 136, wherein the ultrasonic transducer 126 applies ultrasonic energy to the local anesthetic 100, thereby producing a nebulized local anesthetic 100 which is carried by the application of air to the delivery channel 124, similar to FIG. 3A.

In a second operational state, such as EFFECTIVE STANDBY, similar to FIG. 3B, of the medication delivery apparatus 150, wherein the ultrasonic transducer 126 applies ultrasonic energy to the local anesthetic 100, thereby producing a nebulized local anesthetic, which remains in the inner housing. In the embodiments of FIGS. 4A and 4B, the ON operational state and the EFFECTIVE STANDBY operational state may be selected by any technique including the state of a valve, such as the valve 138 in FIGS. 3A through 3C, such that the valve 138 closing in response to negative pressure at the vacuum port, e.g., the application of a vacuum (VAC) causes the EFFECTIVE STANDBY operational state.

The order of execution or performance of the methods and operations illustrated and described herein is not essential, unless otherwise specified. That is, elements of the methods and flows may be performed in any order, unless otherwise specified, and that the methods may include more or less elements than those disclosed herein. For example, it is contemplated that executing or performing a particular step before, contemporaneously with, or after another step are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A medication delivery apparatus for the application of a local anesthetic to a treatment site, the medication delivery apparatus comprising:
    a housing;
    a reservoir configured to contain the local anesthetic, the reservoir disposed in fluid communication with a supply channel and a circulation channel;
    a nebulization housing including a lower chamber and an upper chamber; the lower chamber being disposed in fluid communication with the supply channel and the circulation channel;
    a fluid circuit being defined by flow from the reservoir to the supply channel to the lower chamber to the circulation channel;
    an upper channel being disposed in fluid communication with an airflow channel and a delivery channel;
    an ultrasonic transducer positioned in the lower chamber, the ultrasonic transducer configured to generate, upon energization, ultrasonic energy;
    a control valve interposed between a source of positive pressure air and the airflow channel, the control valve configured to selectively apply air to the airflow channel;
    a medical device coupling located at a distal end of the delivery channel, the medical device coupling being accessible externally of the housing; the housing being sized so as to be securable to a hand-held medical device via the medical device coupling;

the reservoir, the supply channel, the circulation channel, the nebulization housing, the fluid circuit, the upper channel, the airflow channel, the delivery channel, and the control valve being located in the housing; the control valve being controllable by a controller, the controller being externally positioned on the housing;

a first operational state of the control valve, wherein the control valve is open, wherein the local anesthetic is configured to circulate from the reservoir to the lower chamber, wherein the ultrasonic transducer is configured to apply ultrasonic energy to the local anesthetic, thereby producing a nebulized local anesthetic adapted to be carried by the application of air to the delivery channel; and a second operational state of the control valve, wherein the control valve is closed, wherein the local anesthetic is configured to circulate from the reservoir to the lower chamber, wherein the ultrasonic transducer is configured to apply ultrasonic energy to the local anesthetic, thereby producing a nebulized local anesthetic adapted to remain in the upper chamber.

2. The medication delivery apparatus as recited in claim 1, further comprising the local anesthetic, wherein the local anesthetic further comprises lidocaine.

3. The medication delivery apparatus as recited in claim 1, further comprising the local anesthetic, wherein the local anesthetic further comprises 4% lidocaine.

4. The medication delivery apparatus as recited in claim 1, wherein the reservoir has a volume from about 5 ml to about 250 ml.

5. The medication delivery apparatus as recited in claim 1, further comprising a heating element associated with the reservoir, the heating element configured to heat the local anesthetic.

6. The medication delivery apparatus as recited in claim 1, further comprising a heating element associated with the reservoir, the heating element configured to heat the local anesthetic to a temperature from about 50° F. (10° C.) to about 105° F. (40.5° C.).

7. The medication delivery apparatus as recited in claim 1, further comprising a heating element associated with the reservoir, the heating element being a heating coil.

8. The medication delivery apparatus as recited in claim 1, wherein the lower chamber and the upper chamber are integrally formed as a single chamber.

9. The medication delivery apparatus as recited in claim 1, wherein the lower chamber has a volume from about 5 ml to about 250 ml.

10. The medication delivery apparatus as recited in claim 1, wherein the upper chamber has a volume from about 5 ml to about 250 ml.

11. The medication delivery apparatus as recited in claim 1, the fluid circuit providing for circulation from the reservoir to the supply channel to the lower chamber to the circulation channel to the reservoir.

12. The medication delivery apparatus as recited in claim 1, wherein the ultrasonic transducer further comprises a device that uses a piezoelectric transducer to produce ultrasonic waves.

13. The medication delivery apparatus as recited in claim 1, wherein the ultrasonic transducer is configured to operate at 40 kHz to 2.5 MHz.

14. The medication delivery apparatus as recited in claim 1, wherein the control valve further comprises a 0.2 lbs to 250 lbs pressure regulator.

15. The medication delivery apparatus as recited in claim 1, wherein the source of positive pressure air further comprises an air compressor.

16. The medication delivery apparatus as recited in claim 1, wherein the source of positive pressure air is configured to provide air pressure from about 0.2 psi to 25 psi.

17. A medication delivery apparatus for the application of a local anesthetic to a treatment site, the medication delivery apparatus comprising:

a housing;

an outer housing having a receiving chamber;

an inner housing configured to insert into the receiving chamber of the outer housing and releasably engage therewith, the inner housing thereby having an engaged position within the outer housing, the inner housing having prongs for a power connection with the outer housing;

the inner housing including a reservoir configured to contain the local anesthetic, the local anesthetic being provided in a pre-measured amount;

an upper channel being disposed in fluid communication with an airflow channel and a delivery channel, the upper channel traversing the outer housing and the inner housing in the engaged position;

an ultrasonic transducer positioned in the inner housing, the ultrasonic transducer configured to generate, upon energization, ultrasonic energy;

the inner housing and ultrasonic transducer being configured for single-use;

a medical device coupling located at a distal end of the delivery channel, the medical device coupling being accessible externally of the housing; the housing being sized so as to be securable to a hand-held medical device via the medical device coupling;

the outer housing, the inner housing, the upper channel, the airflow channel, the delivery channel, and a control valve being located in the housing;

the control valve being controllable by a controller, the controller being externally positioned on the housing;

a first operational state of the medication delivery apparatus wherein positive pressure air is configured to traverse the upper channel, wherein the ultrasonic transducer is configured to apply ultrasonic energy to the local anesthetic, thereby producing a nebulized local anesthetic adapted to be carried by the application of air to the delivery channel;

a second operational state of the medication delivery apparatus, wherein the ultrasonic transducer is configured to apply ultrasonic energy to the local anesthetic, thereby producing a nebulized local anesthetic adapted to remain in the inner housing; and the control valve interposed between a source of positive pressure air and the upper channel, the control valve configured to selectively apply air to the upper channel and the delivery channel, the control valve being open in the first operational state and closed in the second operational state.

18. The medication delivery apparatus as recited in claim 17, wherein the local anesthetic further comprises lidocaine.

19. The medication delivery apparatus as recited in claim 17, wherein the local anesthetic further comprises 4% lidocaine.

20. The medication delivery apparatus as recited in claim 17, wherein the reservoir has a volume from about 5 ml to about 250 ml.

21. The medication delivery apparatus as recited in claim 17, further comprising a heating element embedded in the outer housing proximate the inner housing, the heating element configured to heat the local anesthetic.

22. The medication delivery apparatus as recited in claim 17, further comprising a heating element embedded in the outer housing proximate the inner housing, the heating element configured to heat the local anesthetic to a temperature from about 50° F. (10° C.) to about 105° F. (40.5° C.).

23. The medication delivery apparatus as recited in claim 17, further comprising a heating element embedded in the outer housing proximate the inner housing, the heating element being a heating coil.

24. A medication delivery apparatus for the application of a local anesthetic to a treatment site, the medication delivery apparatus comprising:

a housing;

a reservoir configured to contain the local anesthetic, the reservoir disposed in fluid communication with a supply channel and a circulation channel;

a nebulization housing including a lower chamber and an upper chamber;

the lower chamber being disposed in fluid communication with the supply channel and the circulation channel;

an upper channel being disposed in fluid communication with an airflow channel and a delivery channel;

an ultrasonic transducer positioned in the lower chamber, the ultrasonic transducer configured to generate, upon energization, ultrasonic energy;

a control valve interposed between a source of positive pressure air and the airflow channel, the control valve configured to selectively apply air to the airflow channel;

a medical device coupling located at a distal end of the delivery channel, the housing being sized so as to be securable to a hand-held medical device via the medical device coupling;

the reservoir, the supply channel, the circulation channel, the nebulization housing, the upper channel, the airflow channel, the delivery channel, and the control valve being located in the housing;

the control valve being controlled by a controllable, the controller being externally positioned on the housing;

a first operational state of the control valve, wherein the control valve is open, wherein the control valve is configured to apply air to the airflow channel, wherein the local anesthetic is configured to circulate from the reservoir to the lower chamber, wherein the ultrasonic transducer is configured to apply ultrasonic energy to the local anesthetic, thereby producing a nebulized local anesthetic adapted to be carried by the application of air to the delivery channel; and a second operational state of the control valve, wherein the control valve is closed, wherein the local anesthetic is configured to circulate from the reservoir to the lower chamber, wherein the ultrasonic transducer is configured to apply ultrasonic energy to the local anesthetic, thereby producing a nebulized local anesthetic adapted to remain in the upper chamber.

* * * * *